Figure 5:
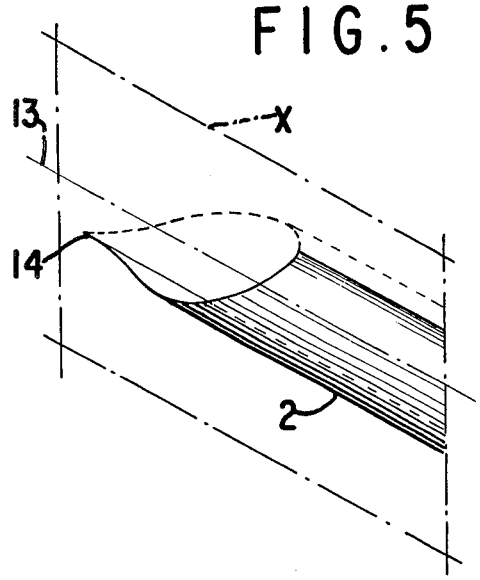

United States Patent [19]

Nordstrom et al.

[11] 4,020,835
[45] May 3, 1977

[54] CATHETER PLACEMENT ASSEMBLY

[75] Inventors: Cai Gustav Rabbe Nordström, Munich; Peter Veerhoff, Bingen (Rhine), both of Germany

[73] Assignee: Boehringer Ingelheim GmbH, Ingelheim am Rhein, Germany

[22] Filed: Feb. 11, 1976

[21] Appl. No.: 657,267

Related U.S. Application Data

[63] Continuation-in-part of Ser. No. 497,701, Aug. 15, 1974, abandoned.

[30] Foreign Application Priority Data

Feb. 12, 1975 Germany .......................... 2505790
Aug. 16, 1973 Germany .......................... 2341297
Nov. 28, 1973 Germany .......................... 2359134

[52] U.S. Cl. .................... 128/214.4; 128/DIG. 26; 128/133; 128/221
[51] Int. Cl.² ......................................... A61M 5/00
[58] Field of Search .............. 128/214.4, 221, 347, 128/348, 133, DIG. 16, DIG. 26

[56] References Cited

UNITED STATES PATENTS

| | | | |
|---|---|---|---|
| 3,030,953 | 4/1962 | Koehn ........................... | 128/214.4 |
| 3,167,072 | 1/1965 | Stone et al. ..................... | 128/133 |
| 3,288,137 | 11/1966 | Lund ................................ | 128/133 |
| 3,313,299 | 4/1967 | Spademan ...................... | 128/214.4 |
| 3,352,306 | 11/1967 | Hirsch ............................ | 128/214.4 |
| 3,399,674 | 9/1968 | Pannier et al. .................. | 128/214.4 |
| 3,459,183 | 8/1969 | Ring et al. ...................... | 128/214.4 |
| 3,734,095 | 5/1973 | Santomieri ..................... | 128/214.4 |
| 3,766,916 | 10/1973 | Moorehead et al. ........... | 128/214.4 |
| 3,812,851 | 5/1974 | Rodriquez ...................... | 128/133 |
| 3,827,434 | 8/1974 | Thompson et al. ............. | 128/214.4 |

FOREIGN PATENTS OR APPLICATIONS 434,028 11/1911 France .............................. 128/221

*Primary Examiner* — Dalton L. Truluck
*Attorney, Agent, or Firm* — Hammond & Littell

[57] ABSTRACT

A vein catheter placement assembly consisting essentially of a catheter unit and a puncture needle unit longitudinally slidably positioned in the catheter. The puncture needle unit comprises a hollow longitudinally grooved puncture needle, and a finger-grip attached to the end of the needle remote from the needle point; the finger-grip, which extends laterally at an angle to the needle plane and thereby facilitates proper insertion of the assembly into a vein, is hollow and made of transparent material, providing a visible receptacle for the reception of blood released upon puncture of a vein by the needle point. The catheter unit comprises a catheter and, communicating therewith and laterally extending therefrom, a tube adapted to be connected to an infusion liquid source.

27 Claims, 14 Drawing Figures

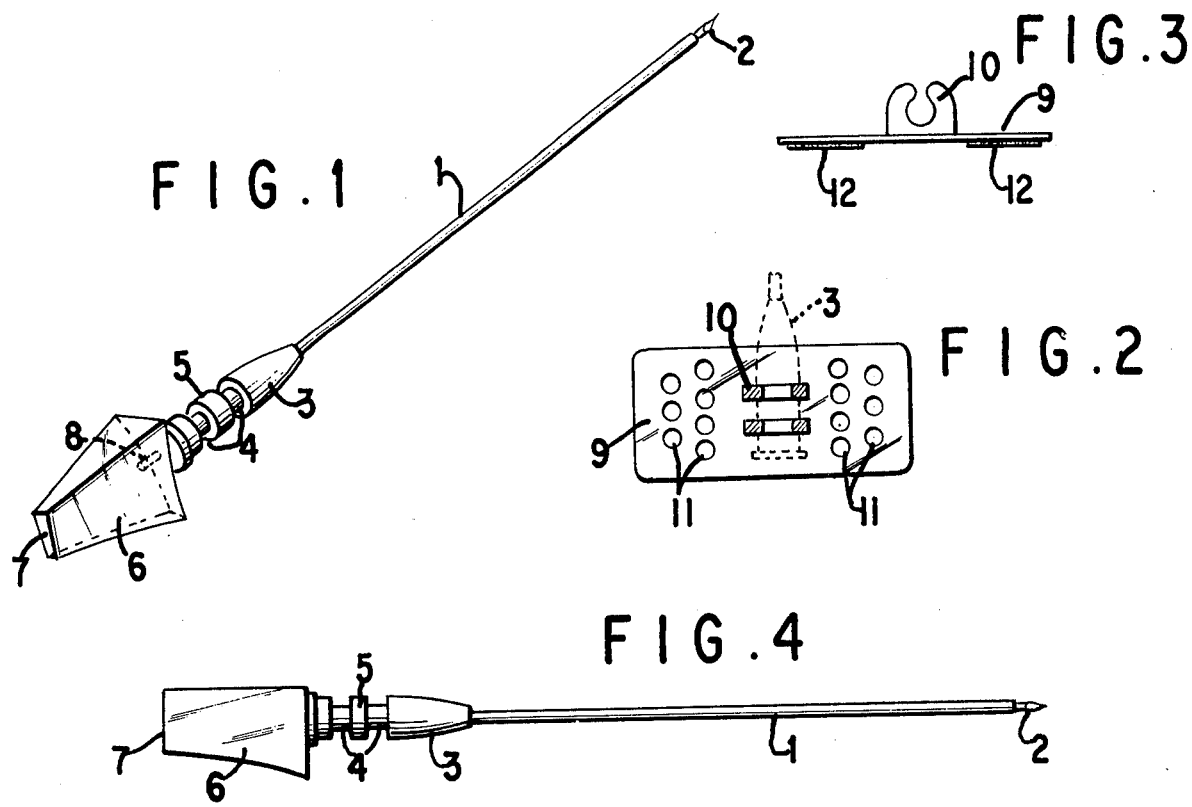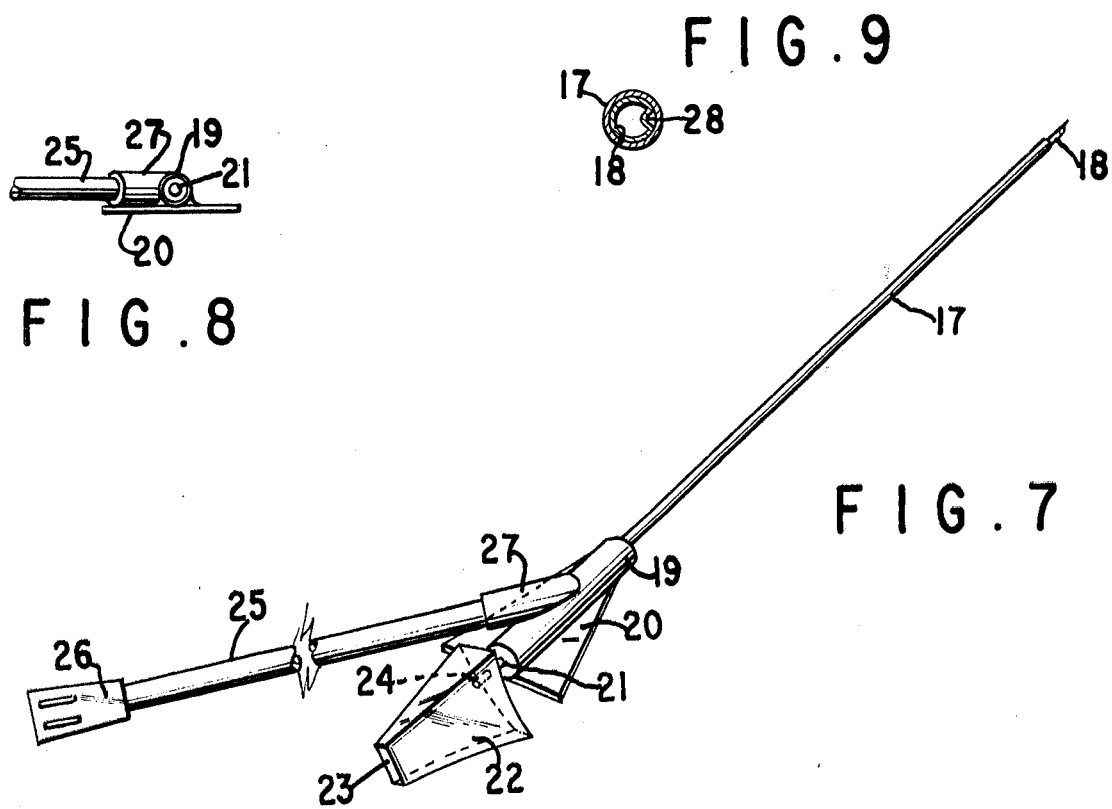

CATHETER PLACEMENT ASSEMBLY

This is a continuation-in-part of copending application Ser. No. 497,701 filed Aug. 15, 1974, now abandoned.

BACKGROUND OF THE INVENTION

Vein catheters are usually inserted into the vein of a patient by means of a hollow needle which is then withdrawn to avoid damage to the walls of the vein. The catheter remains fixed in the patient and is then connected to a source of infusion liquid. Fixing can conveniently be effected by means of flaps on the catheter which are pressed against the skin and, for example, as described in German Offenlegungsschrift No. 1,929,050, are secured there with adhesive tape. It has been proposed that these flaps should be pivotable about the catheter so that they can be gripped and can thus facilitate insertion of the catheter. However, it is very expensive from a manufacturing standpoint to fit such pivotable flaps; and the presence of the flaps renders the satisfactory packing of the device more difficult. In addition, due to their relatively large surface area, the sterilization of such catheters, which is nowadays normally effected by irradiation, is generally more expensive than with devices having smaller surface areas.

Furthermore, when inserting the catheter it is a matter of considerable importance to ensure that the needle is correctly positioned in the vein in order to avoid damage to the walls of the vein and resulting pain to the patient. During insertion, it is generally desirable that the point of the needle should be maintained in the top or, more preferably, the bottom position when viewing the needle from its pointed end. The correct insertion of the needle is rendered difficult by the fact that the point of the needle is invisible after it has penetrated the skin, so that the exact position of the point of the needle, for example, whether the point is being maintained in the desired top or bottom position, is not known to the person inserting the needle. Moreover, since the needle must be inserted into the skin at an acute angle, allowance must be made when inserting the needle for the oblique movement of the needle and this introduces further difficulties in locating the needle exactly in a particular vein.

OBJECTS OF THE INVENTION

It is an object of the present invention to provide a vein catheter placement assembly wherein the above-mentioned flaps in the prior art devices are replaced as insertion aids by a finger-grip which is so shaped and constructed as to facilitate the correct positioning of the catheter in the vein.

Another object of the present invention is to provide a vein catheter placement assembly which avoids contact between the manipulator's hands and the patient's blood, and thus substantially eliminates the danger of infection.

A still further object of the present invention is to provide a vein catheter placement assembly which substantially eliminates the danger of air embolisms.

Still other objects and advantages of the present invention will become apparent as the description thereof proceeds.

DESCRIPTION OF THE INVENTION

The present invention relates to a novel vein catheter placement assembly, as well as to a novel puncture needle unit for use in conjunction therewith.

According to one feature of the present invention, there is provided a hollow pointed puncture needle for use in a vein catheter placement assembly, which has a finger-grip attached to the end of said needle remote from the needle point, the said finger-grip having two essentially concave surfaces which are adapted for gripping by the thumb and finger, with the thumb uppermost, and which are so angled with respect to the needle that, when thusly gripped, the plane of the finger-grip (as hereinafter defined) is at an angle of at least 45° to the plane of the needle (as hereinafter defined).

According to a further feature of the present invention, there is provided a vein catheter placement assembly comprising a vein catheter, and a hollow, pointed puncture needle according to the invention, as hereinbefore defined, axially slidable within the said catheter.

The expression "plane of the needle" is used herein to indicate the plane passing through the axis of the needle which intersects the point of the needle. As explained above, when manipulating the needle it is generally desirable that the needle point be maintained in the top or, more preferably, the bottom position when viewing the needle from its pointed end. It is thus generally desirable that the plane of the needle should be maintained approximately vertical.

The expression "plane of the finger-grip" is used herein to indicate the plane passing through the axis (or extended axis) of the needle which intersects the central point of the narrow side of the finger-grip. When the concave surfaces have a common edge, that is, when they meet at the narrow side of the hand-grip, the central point is the midpoint along the length of this common edge. It is this midpoint which is intersected by the plane of the finger-grip. When the concave surfaces do not have a common edge, that is, when they do not meet, but remain spaced apart at the narrow side of the hand-grip, the central point is a point halfway between the mid-points along the lengths of the edges of the concave surfaces situated at the narrow side of the fingergrip.

In accordance with the invention, when the fingergrip is gripped between the thumb and finger (the thumb and forefinger being in general conveniently used) with the thumb being uppermost, the plane of the finger-grip is at an angle of at least 45° to the plane of the needle. When using the needle to puncture a vein, the manipulator cannot see the position of the point of the needle following piercing of the patient's skin; but, provided that the plane of the fingergrip is maintained at an approximately constant angle to the vertical, the position of the needle point when viewed from the pointed end of the needle will remain approximately the same. Thus, for example, if the angle between the plane of the finger-grip and the plane of the needle is about 75°, a generally preferred angle, and if upon first inserting the needle point the plane of the finger-grip is held at an angle of about 75° from the vertical, then the point of the needle will be approximately at the bottom position when viewing the needle from the pointed end. Upon continuing the puncturing operation, provided the plane of the finger-grip is maintained at an angle of about 75° to the vertical, the point of the needle will remain in approximately the desired bottom position. The precise angle between the plane of the fingergrip and the plane of the needle will depend upon the precise shape of the essentially concave surface of the finger-grip. The purpose is thus to adapt an angle which provides a comfortable manipulating position when gripping by the thumb and finger, with the thumb uppermost, and maintaining the plane of the needle vertical. The position which is most comfortable will depend upon the shaping of the essentially concave surfaces. In general, an angle of from 45° to 90° between the plane of the finger-grip and the plane of the needle is desired. As stated above, a generally preferred angle has been found to be about 75°.

In accordance with one particularly preferred feature of the present invention, the finger-grip provides a receptacle for the reception of blood released upon puncture of a vein by the needle. Thus, when the finger-grip is a receptacle, and upon puncturing a vein, blood can flow through the needle into the receptacle. To facilitate the flow of blood, the finger-grip is advantageously provided with at least one air-permeable surface through which air can be displaced upon reception of blood therein. Also the fingergrip preferably has at least one transparent or translucent wall, whereby blood received into the finger-grip is visible to the manipulator of the needle, thereby providing an indication of when a vein has been successfully punctured. Fluting or facetting on the transparent or translucent wall or walls can, if desired, be provided to facilitate the observation of blood received into the finger-grip.

The finger-grip which also serves as a receptacle for blood from a punctured vein represents an important aspect of the present invention.

In one embodiment of the present invention, the finger-grip has a three-sided cross-section in a plane at right angles to the plane of the needle, two of the said sides providing the essentially concave surfaces and the third side joining the non-common edges of the essentially concave surfaces. The said third side can be flat, convex or concave as desired. When the finger-grip is in this form, it is advantageously so shaped that straight lines joining the corner points of the finger-grip cross-section form the approximate shape of an isosceles triangle. In one preferred shape of the finger-grip, the two straight lines extending across the concave surfaces form an angle of about 30° with one another and an angle of about 75° with the third straight line. The finger-grip preferably tapers towards the end thereof remote from the point of the needle.

In another embodiment, the finger-grip has a four-sided cross-section in a plane at right angles to the plane of the needle, two opposite sides providing the essentially concave surfaces, a third narrow side joining adjacent edges of the concave sufaces, and a fourth side joining the more spaced apart edges of the concave surfaces. The finger-grip thus has an approximately trapezoidal cross-section. Again, the finger-grip preferably tapers towards the end thereof remote from the point of the needle.

Figure 6:
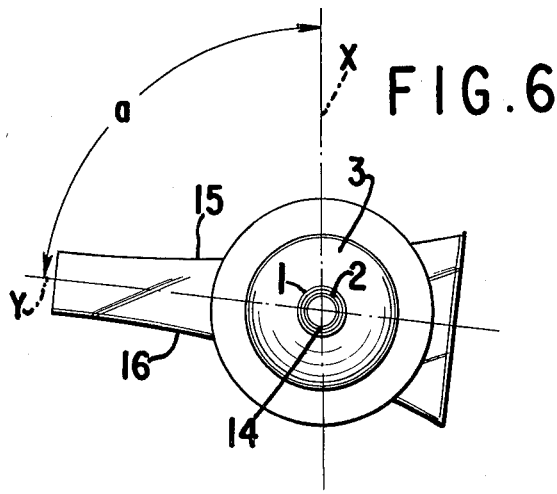

In still another embodiment, the concave gripping surfaces are carved out of a rounded body, such as a sphere, or an optionally flattened rotation ellipsoid, or a paraboloid. Here again, the finger-grip is advantageously formed in such a way that its grip surfaces are particularly adapted for gripping by the thumb and index finger, with the thumb uppermost. Because they are carved out of a rounded body, the grip surfaces are linked together, each along their upper and lower edges extending the direction of the needle axis, by two preferably convex "base planes", which, however, do not have to be of equal size. In the extreme case, one of the base planes has shrunk to a line; for this case the embodiment according to FIG. 6 is applicable.

The two "residual planes" of the finger-grip, i.e. those linking together the two edges facing towards the needle end and the edges opposite those edges of the grip-surfaces (proximal and distal limiting plane of finger-grip, respectively), are preferably shaped convex and do not have to be of equal size. According to a preferred embodiment, the proximal residual plane is smaller than the distal one; thus the finger-grip tapers towards the proximal end. The concave grip surfaces, carved out of the rounded body in plate-like manner, are advantageously arranged in such a way that a section defined by symmetric lines running through the needle axis in needle direction of the base planes facing each other, the so-called "finger-grip plane Y" forms an angle of 45° to 90°, preferably approx. 75° (see FIG. 4) with the plane defined by the line running through the needle axis and the needle bottom to the needle point, i.e. the so-called "needle plane X".

Those chords extending over the concave grip surfaces which link the two base planes to each other, may be parallel or converge toward each other, where in the case of the present embodiment they intersect behind the smaller base plane (towards which they extend). At the point of intersection they form preferably an angle of 30°, and an angle of 75° with the chord extending over the bigger base plane. The chords which extend over the grip surfaces at right angles to the above-mentioned chords, i.e. in the direction of the needle axis linking the two residual planes, may be parallel or converge toward each other as well. In the latter case one of the so-called "residual planes" is smaller than the other (preferably the proximal one), i.e. the grip tapers preferably towards the proximal end.

The catheter unit is made of flexible plastic, preferably of Teflon, since this material does not cause thrombosis and is X-ray permeable.

As indicated above, flaps have been employed in previous catheters to attach the catheter unit to the skin after insertion of the assembly into a vein.

It is possible to avoid the use of flaps by replacing these with a separate fixing member which is attached to the catheter unit when required. This fixing member may, for example, comprise a base, advantageously a rectangular base of sheet material, for example, in the form of a disc which can be made of metal, for example aluminum, but preferably made of plastic. The underside of the base is conveniently provided with means, for example an adhesive layer, for securing the fixing member to the skin. On the upper side, preferably near the middle, of the said base a fixing unit is provided, said unit comprising claws, for example four claws facing one another in pairs, made of resilient material. Where two pairs of claws are used, the pairs are preferably not immediately adjacent to one another, but are spaced a distance of a few millimeters apart, leaving a space between them. The cathether unit is preferably adapted to co-operate with the above-described fixing units. Thus, the catheter unit is preferably provided at its rear end with a thickened portion having at least one means for co-operation with the fixing unit. When the fixing unit has two pairs of claws, two grooves are provided which extend around the thickened portion of the catheter with a ring of the thickened portion situated between the grooves. The width of this ring is such that it fits precisely into the above-indicated space between the top two pairs of claws of the fixing unit.

For the purpose of attaching the fixing unit to the catheter, the latter is placed on top of the claws. By pressing down the catheter the two pairs of claws are forced apart as a result of their elasticity, thus allowing the catheter to pass between them. After insertion of the catheter, the claws spring back to their original positions and grip the catheter at its groove, since the space enclosed by each pair of claws is approximately circular, and the diameter thereof corresponds approximately to that of the grooves of the catheter. In this manner, the claws fit snugly against the catheter and grip it as securely as possible.

Simultaneously with the penetration of the grooves between the pairs of claws upon pressing down the catheter, the ring located between the grooves is pressed down between the grooves into the space between the two pairs of claws. This leads to a very firm connection between the fixing unit and catheter which cannot be detached by accidental or chance movements.

While the claws can, if desired, be so arranged as to locate the catheter in a position generally parallel to the skin of the subject, it is in general preferable that two pairs of claws be provided which, in use, support the vein catheter at an acute angle to the skin of the subject. This can be achieved by constructing the fixing unit with one pair of claws at a higher level than the second pair of claws.

The base of the above-described fixing member can also be provided with a plurality of holes on either side of the fixing unit. These holes thus make the fixing unit, which must be horizontally rigid, movable or flexible in the vertical direction. Also, after use, a chemical solvent can be dosed into and trickled through the holes in order to facilitate removal of the base from the skin.

The use of a fixing member separate from the actual catheter not only has the advantage of lower cost in manufacturing, packing and sterilization. In addition, the device can be caused to lie completely flat on the patient's arm, so that no injuries can occur as a result of pressure applied to the apparatus, or can be held at an acute angle, as desired, by using an appropriately constructed fixing member.

The device according to the present invention can also be adapted to provide the possibility, during continuous infusions, for example from a continuous drip bottle, of injecting other liquids, such as medicament solutions, without having to puncture a further vein or to break off the infusion. In this embodiment, the catheter is fitted with a connector whereby an inlet for infusion liquid into the catheter with the needle positioned in the catheter is provided. The said inlet for infusion liquid is preferably at an acute angle to the longitudinal axis of the catheter and can be connected through an adaptor to a reservoir of infusion liquid. In a preferred embodiment, a tubular distributor is used, and the vein catheter terminates inside the tubular distributor before the acute-angled inlet for transfusion liquid so that transfusion liquid entering through the inlet immediately flows into the catheter. The hollow needle, however, passes completely through the distributor to the finger-grip which is located at the end of the needle remote from its point. In order to allow a rapid removal of the needle after the catheter has been placed, the connector preferably has a selfsealing closure member, which can conveniently be made of rubber, through which the needle is withdrawn following puncturing of the vein. The self-sealing closure member then seals the end of the connector and thereby prevents the escape of infusion liquid after the needle has been removed.

In use, a very soft plastic tube approximately 20 to 25 cm long may be connected, for example by fusion, to the infusion liquid inlet of the connector and thus to the catheter. In turn, this tube may have at its end remote from the catheter a female connection cone, for example, a Luer or Luer-Lok cone, which is intended for connection to a storage vessel for infusion liquid. In this manner by using the connection cone, for example, when connecting or replacing the storage vessel, no injuries to the walls of the vein can take place as a result of compressive or tensile stresses. A similar effect is also obtained by using a flexible catheter, for exaple made of Teflon, since the sharp tip of the puncture needle need no longer remain in the vein during the transfusion process.

If, in addition to the transfusion liquid passing into the catheter from the reservoir via the tube and adaptor, it is desired to inject a further liquid, this can be effected, for example, by means of a syringe through the self-sealing closure member which automatically seals on removing the puncture needle. Thus it is possible to inject any desired liquid into the catheter simultaneously with the introduction of infusion liquid without the need for any further contact with the patient.

According to a further preferred embodiment of the present invention, a base, for example, a flat sheet in the shape of a webbed-foot of an aquatic bird, is provided on the underside of the above-mentioned connector fitted to the catheter. Such a base facilitates the attachment or fixing of the apparatus to the arm by means of an adhesive material, such as adhesive tape. In this manner, as a result of the simplified attachment of the catheter through the connector to a storage vessel for infusion liquid, a flat construction of the device is facilitated, so that the position of the catheter on the patient's arm is also improved.

According to a further particularly preferred embodiment of the invention, the catheter fitted with a connector, as hereinbefore described, is used together with a hollow puncture needle having an external longitudinally extending groove, whereby in use infusion liquid can be introduced through the inlet for infusion liquid along the groove to the point of the needle while the needle is in position in the catheter. Conveniently, the groove extends the length of the needle parallel to the axis of the needle and is preferably situated at an angle of 45° to the plane of the needle. The principal advantage of the groove is that, in use, infusion liquid can be introduced along the catheter to the point of the needle prior to use of the needle to puncture the vein. Then, upon vein puncture with consequent flow of blood along the inside of the needle an air-free system is obtained. As the needle is removed following vein puncture, the space occupied by the needle is filled by blood flowing from the vein and the air-free system is maintained. In practice, the maintenance of an air-free system in this way is of importance in that the danger of air-embolisms occuring is avoided.

The use of a grooved needle in conjunction with a catheter fitted with a connector, as hereinbefore described, represents an important aspect of the present invention.

Other advantageous structural elements, such as are known from other apparatus, for example, the use of an X-ray-opaque Teflon catheter, indicating the cannular size on the connecting cone as well as the so-called Luer-Lok system for connecting 3-way cocks or tubes, can be also used with the device according to the invention. The device can be made in the usual sizes as well as constructions for use in special veins such as the V.subclavia, V.saphena magna or V. femoralis, or in the veins of the head.

The apparatus is advantageously packaged in deep-drawn plastic foil with a so-called "peel-back."

The catheter placement assembly according to the present invention will now be described with reference to the accompanying drawings, which illustrate various preferred embodiments of the invention. These drawings are not to be deemed limitative of the invention in any manner thereof.

In the accompanying drawings, where like reference numerals identify like parts, FIGS. 1 to 6 illustrate a vein catheter according to the invention provided with a fixing member for attachment to the skin of a patient. FIGS. 7 to 9 illustrate a vein catheter according to the invention provided with a connector, and FIGS. 10 to 14 illustrate a vein catheter of the type illustrated in FIGS. 1 to 6, but with alternative forms of the finger-grip.

Referring first to the embodiment illustrated in FIGS. 1 to 6, FIG. 1 is a view of a catheter placement assembly in accordance with the invention shown diagonally from the rear. A catheter 1 has a puncture needle 2 axially positioned therein. The catheter has a thickened portion 3 in which are formed two grooves 4 separated by the ring 5. At the end 8 of the puncture needle remote from the point, a finger-grip 6 of approximately trapezoidal cross-section is provided. The finger-grip is hollow and forms a receptacle, the needle being mounted in the finger-grip, whereby, upon puncturing a vein, blood will flow along the hollow needle and into the receptacle. The rear end 7 of the finger-grip is an air-permeable membrane. The remaining walls of the handgrip are made of facet-like fluted artificial glass.

FIG. 2 provides a plan view of the fixing member. A base 9 is provided by a disc on which are mounted two pairs of claws 10 between which the catheter can be clamped. The disc is provided with holes 11 which allow some vertical movement of the claws 10 when the member is fixed to the skin of a patient.

FIG. 3 provides a side view of the fixing member. The pairs of claws 10 are arranged to effect fixing of the catheter parallel to the skin of the patient. An adhesive layer 12 is provided on the underside of disc 9 to facilitate fixing of the disc to the skin of the patient.

FIG. 4 provides a side view of the catheter placement assembly of FIG. 1.

FIG. 5 provides an enlarged perspective view of the point end of the needle 2. The point 14 of the needle is shown in the bottom position. The letter X indicates the plane of the needle passing through the needle axis 13 and intersecting the point of the needle 14.

FIG. 6 shows the catheter device of FIG. 1 viewed from the pointed needle end. The concave surfaces 15 and 16 of the finger-grip are shown. Also, the plane Y of the handgrip and the plane X of the needle are marked, and $a$ indicates the angle between X and Y, which in the embodiment illustrated is approximately 75°. When using the needle to puncture a vein, the finger-grip will be held between the thumb and index finger, with the thumb uppermost, at the approximate angle illustrated in FIG. 6, that is, with the plane of the needle approximately vertical.

Referring next to the embodiment illustrated in FIGS. 7 to 9, FIG. 7 is a view of the catheter placement assembly diagonally from the rear. The catheter 17 is shown with a puncture needle 18 in position. The catheter 17 is fitted with a plastic connector 19. A thin web-like plastic sheet base 20 is formed on the connector 19. The finger-grip 22 is constructed similarly to the finger-grip of the device illustrated in FIGS. 1, 4 and 5 with an air-permeable wall 23, and is fitted to the end 24 of the needle remote from the needle point. A rubber self-sealing closure member 21 is provided through which the needle can be withdrawn when a vein puncture has been effected. Adapter 27 provides an inlet for infusion liquid through connecting tube 25 made from very soft plastic material connected to adapter 27. The mounted female Luer cone 26 is provided to facilitate the connection of the device to a storage vessel for infusion liquid.

In FIG. 8 the apparatus of FIG. 7 is shown from the rear. The reference numerals are the same as in FIG. 7, so that 19 represents the connector, and 21 represents the rubber self-sealing closure member, while 25 represents the soft connecting tube and 27 represents the adapter.

FIG. 9 shows a cross-section through the catheter and needle of the device. A groove 28 extends along the entire length of the outside of needle 18. Injection liquid can thus be introduced through adapter 27 along the groove 28 to the point of the needle when the needle is in position as shown in FIG. 7 of the drawings.

In the embodiment shown in FIGS. 7 to 9 the angle between the plane of the finger-grip and the plane of the needle is approximately 75°. Thus the finger-grip is fitted to the needle at an angle, as illustrated in FIG. 6 for the previously illustrated embodiment.

Figure 10:
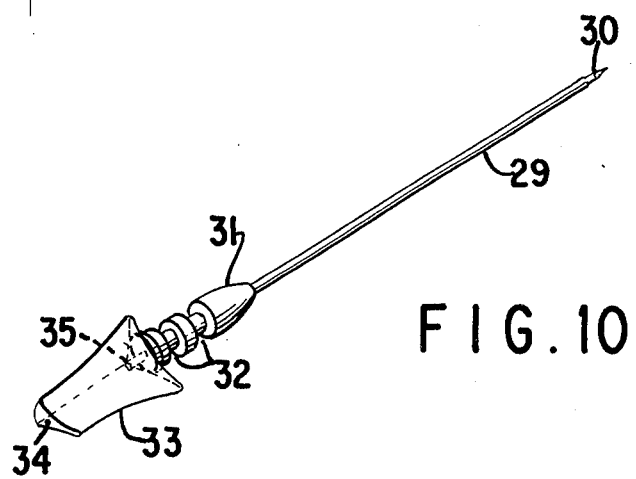

FIGS. 10 through 14 illustrate embodiments with differently shaped finger-grips. FIG. 10 is a view of the device diagonally from the rear. It comprises a catheter 29 with a hollow puncture needle 30 longitudinally slidable therein. The catheter is provided with a thickened portion 31 in which are formed two grooves 32. At the end 35 of the puncture needle remote from the point, a finger-grip 33 of approximately triangular cross-section is provided. The finger-grip is hollow and forms a receptacle for blood from a punctured vein. The rear end 34 of the finger-grip is an air-permeable membrane; the remaining walls of the finger-grip are made of facet-like fluted artificial glass.

Figure 11:
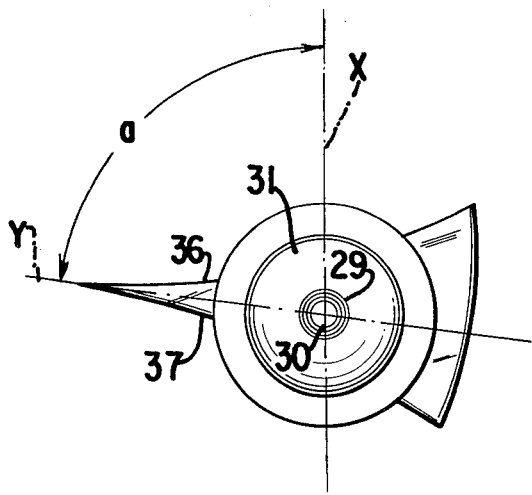

FIG. 11 shows an end-view of the catheter device of FIG. 10. The concave surfaces 36 and 37 are shown. Also, the plane of the finger-grip as well as the plane X of the needle is marked, and $a$ indicates the angle between X and Y which in the embodiment illustrated is approximately 75°.

Figure 12:
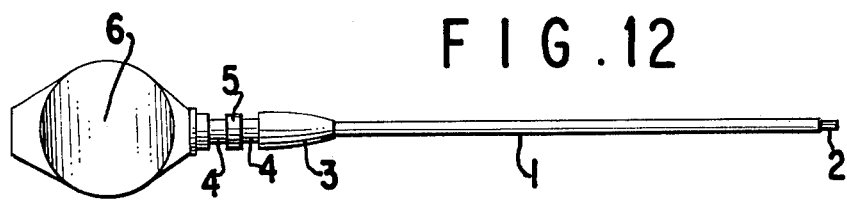
Figure 13:
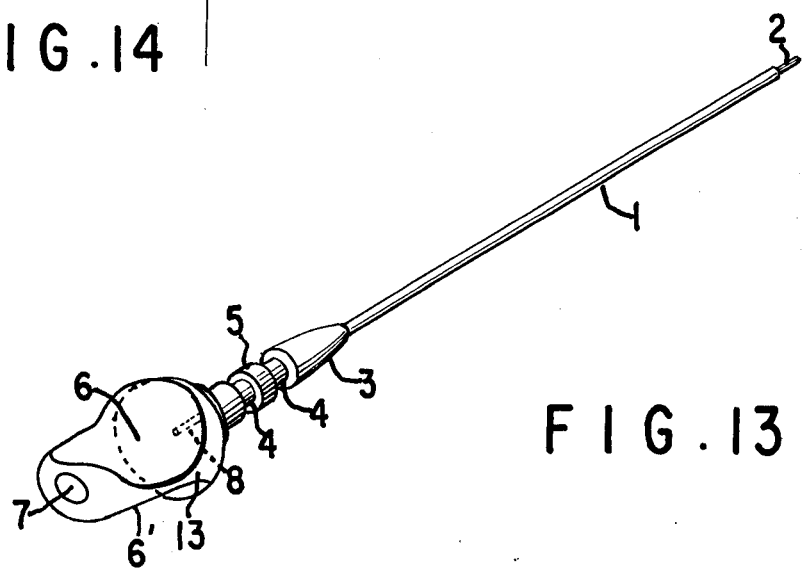

FIGS. 12 and 13 show a catheter placement assembly according to the present invention which is substantially identical in structure to the assembly shown in FIGS. 1 and 4, differing only in the structural embodiment of the fingergrip. In this embodiment the concave gripping surfaces are carved out of a round body, namely an egg-shaped body.

More particularly, FIG. 12 is a top view of the vein catheter placement assembly where the concave plate-like grip surfaces, i.e. increasing towards the edges, are particularly well recognizable as having been carved out of an egg-shaped body. A catheter 1 carries a needle 2 positioned axially slidable therein, the protruding point of the needle being shown. At the rear end of the catheter, there is the conical thickened portion 3 with the two annular grooves 4 therein, the grooves being separated by a spacing ring 5. 6 is the finger-grip with one of the concave grip surfaces.

FIG. 13 is a perspective view of the device as seen diagonally from the rear. Reference numerals 1 to 6 identify the same parts as in FIG. 1. 7 is the air-permeable membrane inserted into the proximal "residual plane", 8 is the proximal needle end which projects into the hollow fingergrip, and 13 is the smaller of the base planes connecting the two grip surfaces with one another.

Figure 14:
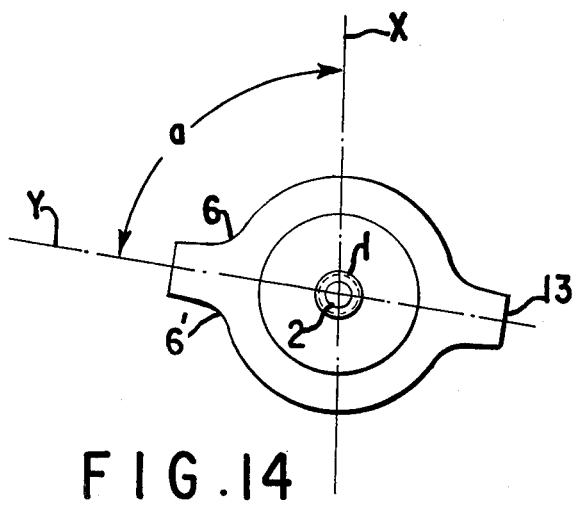

FIG. 14 is a front view of the catheter placement assembly of FIGS. 12 and 13, as seen from the needle point. The concave grip-surfaces 6 and 6' of the finger-grip are shown. Furthermore, the needle plane X, the finger-grip plane Y, as well as the angle a between these planes corresponding to an angle of 75° are shown. The remaining reference numerals identify the same parts as in FIGS. 12 and 13.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. In a vein catheter placement assembly comprising a flexible catheter having a forward end and a rearward end and a puncture needle unit longitudinally slidably positioned within said catheter; said puncture needle unit comprising a hollow tubular puncture needle having a pointed forward end and a rearward end and being open at both ends, said pointed forward end protruding beyond the forward end of the catheter and the rearward end of the puncture needle protruding beyond the rearward end of the catheter, and a finger-grip attached to the rearward end of the puncture needle; the improvement which resides in that said finger-grip extends laterally from the rearward end of said puncture needle in a finger-grip plane which is at an angle substantially intermediate that of 45 to 90° with respect to the needle plane defined by the longitudinal axis of the puncture needle and the point of the puncture needle, and said finger-grip comprising a pair of exterior concave surfaces substantially symmetrically disposed with respect to said finger-grip plane.

2. The catheter placement assembly of claim 1, wherein said finger-grip comprises an interior hollow space in which the rearward end of the hollow puncture needle terminates to provide a receptacle for blood released upon puncture of a vein by the puncture needle.

3. The catheter placement assembly of claim 2, wherein said hollow finger-grip comprises at least one airpermeable surface through which air can be displaced upon reception of blood therein.

4. The catheter placement assembly of claim 2, wherein the hollow finger-grip has at least one transparent of translucent wall, whereby blood flowing into the fingergrip is visible to the manipulator of the assembly.

5. The catheter placement assembly of claim 4, wherein the finger-grip is fluted or facetted on said transparent or translucent wall.

6. The catheter placement assembly of claim 1, wherein said finger-grip extends unilaterally from the rearward end of said puncture needle and has a three-sided crosssection in a plane at right angles to the needle plane, two of the said sides providing the essentially concave surfaces and the third side joining the non-common edges of the essentially concave surfaces.

7. The catheter placement assembly of claim 6, wherein three straight lines joining the corner points of the said cross-section form the approximate shape of an isosceles triangle.

8. The catheter placement assembly of claim 7, wherein two of said three straight lines extending across the concave surface form an angle of about 30° with one another and angles of about 75° with the third straight line.

9. The catheter placement assembly of claim 1, wherein the finger-grip has a four-sided cross-section in a plane at right angles to the needle plane, two opposite sides providing the essentially concave surfaces, a third narrow side joining adjacent edges of the concave surfaces, and a fourth side joining the more spaced apart edges of the concave surfaces.

10. The catheter placement assembly of claim 1, wherein said finger-grip tapers towards the end thereof remote from the point of said needle.

11. The catheter placement assembly of claim 1, wherein the angle between the finger-grip and the needle plane is about 75°.

12. The catheter placement assembly of claim 1, wherein the catheter at its rear end is provided with a thickened portion having at least one annular groove formed therein for co-operation with a fixing member for attaching the catheter to the skin of a patient.

13. The catheter placement assembly of claim 12, wherein said thickened portion of said catheter has two annular grooves formed therein.

14. The catheter placement assembly of claim 12, in combination with a fixing member for attaching the catheter to the skin of a subject.

15. The catheter placement assembly of claim 14, wherein said fixing member comprises resiliently releasable attachment means which engage the grooves formed in said thickened portion of said catheter.

16. The catheter placement assembly of claim 15, wherein said fixing member comprises a base for attachment to the skin of a patient, said base being provided with two pairs of claws made from a resilient material and adapted to engaged two corresponding grooves in the thickened portion of the catheter.

17. The catheter placement assembly of claim 16, wherein said pair of claws are so arranged that, in use, the catheter is supported at an acute angle to said base.

18. The catheter placement assembly of claim 16, wherein the said base is in the form of a disc.

19. The catheter placement assembly of claim 16, wherein the base is made of plastic.

20. The catheter placement assembly of claim 16, wherein said base is provided on its lower side with adhesive means.

21. The catheter placement assembly of claim 20, wherein said adhesive means is adhesive tape.

22. The catheter placement assembly of claim 20, wherein said base contains a plurality of perforations.

23. The catheter placement assembly of claim 1, wherein said catheter is fitted with a connector for providing an inlet for infusion liquid into the catheter with said puncture needle positioned in said catheter, and said puncture needle has an external longitudinal groove which extends over the entire length of the needle, whereby, in use, infusion liquid can be introduced through the inlet for infusion liquid along the groove to the point of the needle while the needle is in position in the catheter.

24. The catheter placement assembly of claim 23, wherein said connector comprises a self-sealing closure member located at the end of the connector remote from the point of the needle through which the needle is, in use, withdrawn following puncture of a vein.

25. The catheter placement assembly of claim 24, wherein said closure means upon withdrawal of the needle provides an inlet means through which a liquid can be injected into said catheter simultaneously with the inroduction of infusion liquid into the catheter through the inlet for infusion liquid.

26. The catheter placement assembly of claim 24 wherein a base is provided on the underside of said connector for attaching to the skin of a patient.

27. The catheter placement assembly of claim 1, wherein said pair of exterior concave surfaces are carved out of a symmetrical round body.

* * * * *